United States Patent [19]

Tanaka et al.

[11] 4,166,174
[45] Aug. 28, 1979

[54] BENZAZOCINE DERIVATIVES AND PROCESS FOR PREPARING THE SAME

[75] Inventors: Sadao Tanaka, Tokyo; Morio Kakimoto, Kawagoe; Yugo Ikeda, Tokyo, all of Japan

[73] Assignee: Chugai Seiyaku Kabushiki Kaisha, Tokyo, Japan

[21] Appl. No.: 806,263

[22] Filed: Jun. 13, 1977

[30] Foreign Application Priority Data

Jun. 24, 1976 [JP] Japan .................................. 51/73789

[51] Int. Cl.$^2$ ........................................... C07D 39/00
[52] U.S. Cl. ................................... 542/401; 542/469; 424/267; 546/15; 546/63; 546/97
[58] Field of Search .................. 260/293.54, DIG. 13; 542/401, 469

[56] References Cited

U.S. PATENT DOCUMENTS

| | | | |
|---|---|---|---|
| 3,449,332 | 6/1969 | Clarke et al. | 542/469 |
| 3,631,051 | 12/1971 | Atsumi et al. | 260/293.54 |
| 3,634,433 | 1/1972 | Moriyama et al. | 542/469 |
| 3,639,407 | 2/1972 | Clarke, Jr. et al. | 260/293.54 |
| 3,639,410 | 1/1972 | Albertson et al. | 260/293.54 |
| 3,793,332 | 2/1974 | Atsumi et al. | 260/293.54 |
| 3,823,149 | 7/1974 | Albertson | 260/293.54 |
| 3,833,595 | 9/1974 | Atsumi et al. | 260/293.54 |
| 3,903,093 | 9/1975 | Kobayashi et al. | 260/293.54 |
| 3,969,468 | 7/1976 | Tamaki et al. | 260/293.54 X |
| 4,022,789 | 5/1977 | Albertson | 260/293.54 |

OTHER PUBLICATIONS

Ziering et al., J. Med. Chem., 13 (1970), pp. 9-13.
Parfit et al., J. Med. Chem., 14 (1971), pp. 565-568.
Archer et al., J. Med. Chem., 7 (1964), pp. 123-127.
Michne et al., J. Med. Chem., 15 (1972), pp. 1278-1281.
Takeda et al., J. Org. Chem., 34 (1969), pp. 4161-4162.
Akkerman et al., Chem. Abst., 74 (1971), #125486.

*Primary Examiner*—Arthur P. Demers
*Attorney, Agent, or Firm*—Browdy and Neimark

[57] ABSTRACT

Benzazocine derivatives represented by the formula

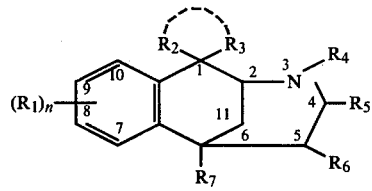

which have an excellent analgesic action and are useful for use in drugs, and a process for preparing the same are disclosed.

22 Claims, No Drawings

BENZAZOCINE DERIVATIVES AND PROCESS FOR PREPARING THE SAME

This invention relates to a benzazocine derivative represented by the formula

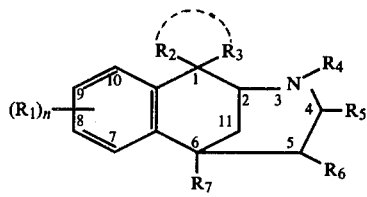

(I)

wherein $R_1$ is hydrogen, halogen, hydroxyl, acyloxyl, lower alkyl, lower alkoxyl or methylene dioxyl; n is an integer of from 1 to 4; $R_2$ and $R_3$ are independently lower alkyl or are bonded to each other directly or through oxygen to represent alicyclic or heterocyclic ring; $R_4$ is hydrogen, lower alkyl which may have a substituent selected from cycloalkyl, phenyl or benzoyl optionally having one or more substituents, or lower alkenyl which may have phenyl as a substituent; $R_5$ and $R_6$ are independently hydrogen or lower alkyl; and $R_7$ is lower alkyl or phenyl, or a salt of the derivative, and a process for preparing the same.

Each of the compounds represented by Formula (I) is novel and has high analgesic action and therefore it is useful for use in drugs.

The compound represented by Formula (I) may be prepared for example, by (a) hydrolizing a compound represented by the formula

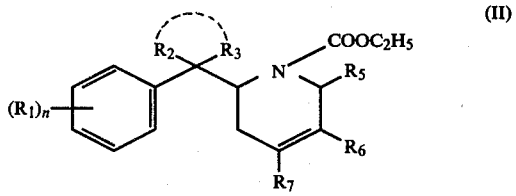

(II)

wherein $R_1$, $R_2$, $R_3$, $R_5$, $R_6$, $R_7$ and n are as defined above under an alkaline condition to remove its ethoxycarbonyl radical and cyclizing the hydrolisate by the action of a mineral acid, or (b) making a mineral acid act on a compound represented by Formula (II) to have hydrolisis and cyclization take place simultaniously thereby giving a compound (III) represented by Formula (I) wherein $R_4$ is hydrogen.

(c) Furthermore, the compound (III) may be prepared by making boron trifluoride etherate act on a compound represented by Formula (II) in the absence of a solvent to give a compound (IV) represented by Formula (I) wherein $R_4$ is $COOC_2H_5$ in a substantially quantitative amount and then making hydrogen bromide in acetic acid act on the compound (IV) whereby the hydrolisis can be easily effected to give the compound (III).

The compound (III) may be reacted with an alkyl or alkenyl halide to give various compounds represented by Formula (I).

(e) The compound represented by Formula (I) may be prepared by hydrolizing the compound of Formula (II) to remove its ethoxycarbonyl radical and then alkylating and cyclizing the hydrolyzed compound.

In effecting the procedure (a), the hydrolysis of the compound of Formula (II) may be carried out in the presence of a strong base such as sodium hydroxide, potassium hydroxide or the like in a dipolar solvent such as ethylene glycol, diethylene glycol, dipropylene glycol or the like at a temperature of from 100° C. to the boiling point of the solvent used for 1-5 hours. The cyclization may be carried out by refluxing the reactant in an aqueous solution of a mineral acid such as hydrogen bromide, hydrogen iodide, phosphoric acid, polyphosphoric acid or the like with or without an organic acid such as acetic acid or propionic acid for 1-15 hours.

In the procedure (b), the cyclization may be carried out in the same manner as in (a).

In effecting the procedure (c), the substantially quantitative cyclization may be carried out by heating a compound of Formula (II) at a temperature of from room temperature to the boiling point of the solvent to be used, more preferably from 50° to 100° C. for 1-5 hours in the presence of a boron halide such as boron trifluoride etherate, boron trifluoride, boron trichloride, boron tribromide or the like with or without using a solvent such as benzene, toluene, methylene chloride or the like.

For the compound of Formula (II) wherein $(R_1)_n$ is methylene dioxy, the cyclization may be preferably effected by using a cyclization accelerator such as p-toluene sulfonic acid in an inert solvent such as benzene, toluene or the like. The compound (IV) obtained according to the procedure (c) may, of course, be hydrolized as in the procedure (a) to give the compound (III).

In order to prepare a compound represented by Formula (I) wherein $R_4$ is not hydrogen from the compound (III) wherein $R_4$ is hydrogen, the following procedure (d), (f) or (g) is used.

(d) The reactant is reacted with a halide represented by the formula $R'_4X$ wherein $R'_4$ is the same as $R_4$ except that hydrogen is omitted and X is halogen in aprotic dipolar solvent such as dimethylformamide, dimethyl sulfoxide or the like in the presence of an alkaline substance such as potassium carbonate, sodium bicarbonate, sodium hydroxide or the like at a temperature of from room temperature to the boiling point of the solvent to be used, preferably 100°–150° C. for 1–6 hours while stirring.

(f) The reactant is reacted with a carboxylic acid of the formula $R'_4COOH$ wherein $R'_4$ is as defined above or its reactive derivative such as acid halide or mixed acid anhydride or the like under the conditions for a conventional amide-formation reaction and then the resulting corresponding N-acyl compound is reduced in a conventional manner.

(g) The reactant is reacted with an aldehyde represented by the formula $R'_4CHO$ wherein $R'_4$ is as defined above in an organic solvent such as methanol, ethanol, chloroform, acetic acid or the like at room temperature or at an elevated temperature on a water bath and then reduced with a metal hydride such as sodium borohydride, sodium borocyanohydride or the like.

Furthermore, in order to prepare the compound represented by the formula (I), without forming the compound (III) as an intermediate, the procedure (e) may be used. This procedure may be effected by reacting the hydrolyzed compound produced by the procedure (a) with a halide in the same manner as in the procedure (d) and cyclyzing the resulting compound as in the procedure (a).

In order to obtain the compound represented by the formula (I) wherein $R_4$ is $CH_3$, it may be prepared in situ by the procedure (h), namely, by suspending or dissolving a metal hydride such as lithium laminium hydride, sodium alminium hydride, sodium bismethoxyethoxy aluminium hydride or the like in an inert solvent such as ethyl ether, tetrahydrofuran, benzene, toluene or the like and adding dropwise the compound (IV) to the suspension or solution to react it at a temperature of from $-10°$ C. to the boiling point of a solvent used, preferably room temperature to $100°$ C., for 10 minutes to several hours to give the compound of Formula (I) wherein $R_4$ is $CH_3$.

Alternatively, the compound of Formula (I) wherein $R_4$ is methyl may be prepared by the procedure (i), namely, by treating the compound of Formula (II) instead of the compound (IV) to convert its N-ethoxycarbonyl radical to N-methyl radical and then cyclizing the N-methyl compound to give the compound of Formula (I) wherein $R_4$ is methyl.

The compound of Formula (II) which is also novel can be prepared, for example, by refluxing a compound represented by the formula

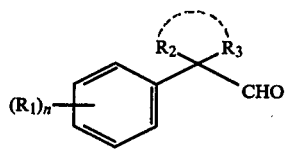

wherein $R_1$, $R_2$, $R_3$ and n are as defined above with urethane in an inert solvent such as benzene, toluene or the like in the presence of a catalytic amount of acid such as boron trifluoride etherate, p-toluene sulfonic acid or the like to give the compound represented by the formula

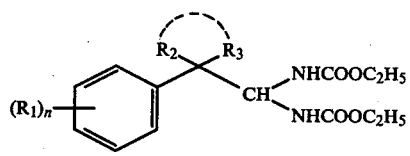

wherein $R_1$, $R_2$, $R_3$ and n are as defined above, adding drop-wise a butadiene derivative solution represented by the formula

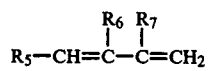

wherein $R_5$, $R_6$ and $R_7$ are as defined above to a solution of the compound (VI) in an inert solvent such as benzene toluene or the like while mildly refluxing and after the completion of the addition, heating the mixture to reflux.

The resulting object compound (I) according to this invention has asymmetric carbon atoms and is present as racemate. However, the racemate can be easily subjected to optical resolution in a conventional manner with the use of a natural acid such as quinic acid, tartaric acid, malic acid, camphoric acid, camphorsulfonic acid, mandelic acid or the like.

The compound (I) can be converted to its mineral acid addition salt such as hydrochloride, sulfate, hydrobromide, phosphate or its organic acid addition salt such as malonate, lactate, malate or acetate.

Each of the compounds represented by Formula (I) is novel and has an excellent analgesic action resembling that of morphine. Further, since it produces no or only a minor degree of levallorphan antagonism and physical dependence, it is very useful for use in drugs.

The present invention will be further illustrated by the following Experiments and Examples, but they are given for illustrative purposes only and are not to be construed as limiting the scope of this invention.

Experiment 1

Analgesic Activities

The compounds of this invention, each of which was used in the form of hydrochloride or lactate, or morphine.HCl (a comparative standard drug) were subcutaneously administered to male mice of ddY strain, 4 weeks old (10 mice/dosage level) and 45 min later, the analgesic activity was determined by the following methods. Each drug was administered at three different dosage levels.

(1) *Acetic Acid Writhing Method* (Koster, R. et al., Fed. Proc., 18, 412, 1959)

Each mouse was intraperitoneally administered with 0.6% acetic acid saline solution and 5 min later the number of writhing syndromes occurring was counted for 5 min.

The dose of test drug that decreased the number of writhing syndromes to half that of control mice was calculated graphically and defined as ED (effective dose).

(2) *Haffner Method* (Green, A. F. et al., Brit. J. Pharmcol. 6, 572, 1951)

The base of mouse's tail was pressed by a dull edged bakelite bar and the pressure loaded on the tail that made the mouse squeak was measured by a mercurymanometer.

The dose of test drug that increased the squeaking pressure to twice that of control mice was calculated graphically and defined as ED (effective dose).

(3) *Hot Plate Method* (Takagi, K. et al., Yakugaku Zasshi (in Japanese), 77, 871, 1957)

Drug-administered mice were placed on a hot plate of $55°$ C. and the time until they jumped was measured individually.

The dose of test drug that increased the time to jump to twice that of control mice was calculated graphically and defined as ED (effective dose).

Results obtained are shown in Table 1.

Table 1

| Test Compounds | Acetic Acid Method | Haffner Method | Hot Plate Method |
|---|---|---|---|
| 1 [structure, (±) form · C$_3$H$_6$O$_3$] | 1.1 | 1.1 | 1.2 |
| 2 [structure, (+) form · C$_3$H$_6$O$_3$] | — | — | 9.0 |
| 3 [structure, (−) form · C$_3$H$_6$O$_3$] | 0.6 | 0.6 | 0.8 |
| 4 [structure · HCl] | 10.5 | 9.1 | 8.2 |
| 5 [structure · HCl] | 1.8 | 1.8 | 2.1 |
| 6 [structure · HCl] | 7.1 | 4.5 | 6.0 |
| 7 [structure · HCl] | 10.5 | 10.0 | 15.1 |
| 8 [structure · HCl] | 7.3 | 8.8 | 11.5 |
| 9 [structure · HCl] | 2.5 | 2.7 | 4.0 |
| 10 Pentazocine · C$_3$H$_6$O$_3$ | 20.0 | 7.0 | 9.6 |
| 11 Morphine · HCl | 0.6 | 0.6 | 0.8 |

Remarks: the figures show ED (mg/kg; subcutaneous injection)

Experiment 2

Levallorphan Antagonism and Physical Dependence (1) *Levallorphan Antagonism* (Blumberg, H. et al., Proc. Soc. Exp. Biol. Med., 123, 755, 1966)

Male mice of ddY strain, 4 weeks old, were used. The compounds of this invention, each of which was used in the form of loctate, or morphine.HCl were subcutaneously administered to mice. Thirty minutes later, the mice were injected subcutaneously with 10 mg/kg of levellorphan. Antagonism by levallorphan to analgesic effect of test compounds was then determined by acetic acid writhing method 15 min after injection with levallorphan.

(2) *Physical Dependence* (Lorenzetti O. J. et al., Arch. Int. Pharmacodyn., 183, 391, 1970; Hosoya, H. et al., Folia Pharmcol. Jap., 53, 120p, 1957; Hosoya, H. et al., Yakuri to Chiryo (in Japanese), 2, 1235, 1974)

Male rats of Sprague Dawlay strain, 5 weeks old, were used. The compounds of this invention or morphine.HCl were subcutaneously administered twice a day for 3 weeks. The administration was started on Thursday, but was withdrawn every Sunday. The daily dose of the test compound was increased weekly (i.e. 20 mg/kg/day for the 1st week, 40 mg/kg/day for the 2nd week and 60 mg/kg/day for the 3rd week). The physical dependence was evaluated in terms of the decrease in the body weight on the day following the day of withdrawal (Sunday) and in terms of the decrease in the body weight induced by 10 mg/kg of levallorphan on the day following the final administration of the test compound.

Results obtained are shown in Table 2.

condenser equipped with a water separater. After cooling, the reaction mixture was washed several times with water and then two times with a saturated sodium bicarbonate aqueous solution and dried over potassium carbonate. After removal of benzene, the residue was recrystallized from chloroformhexane to obtain 108 g of 1,1-bis(ethoxycarbamino)-2-(4-methoxyphenyl)-2-methylpropane as colorless needles.

(m.p.: 127°–128° C.).

Analysis: Calcd. for $C_{17}H_{26}O_5N_2$: C, 60.34; H, 7.74; N, 8.28 (%). Found: C, 60.13; H, 7.85; N, 8.34 (%).

(2) The resulting 1,1-bis(ethoxycarbamino)-2-(4-methoxyphenyl)-2-methylpropane (67.2 g) and boron trifluoride etherate (30 ml) were dissolved in dried benzene (500 ml). Isoprene (15 g) dissolved in 50 ml of dried benzene was added dropwise to the solution over one hour while mildly refluxing and the mixture was refluxed for 3 hours while stirring. After cooling, the reaction mixture was washed several times with water and then washed two times with a saturated sodium bicarbonate aqueous solution and dried over potassium carbonate. After removal of benzene, the residue was further distilled under reduced pressure to obtain 49 g of 1-ethoxycarbonyl-1,2,3,6-tetrahydro-2-[1-(4-methoxyphenyl)-1-methylethyl]-4-methylpyridine as a light yellow syrup.

(b.p.: 158°–160° C./0.5 mmHg).

Analysis: Calcd. for $C_{19}H_{27}O_3N$: C, 71.89; H, 8.57; N, 4.41 (%). Found: C, 71.95; H, 8.85; N, 4.60 (%).

(3) 1-Ethoxycarbonyl-1,2,3,6-tetrahydro-2-[1-(4-methoxyphenyl)-1-methylethyl]-4-methylpyridine (3.17 g) dissolved in 10 ml of dried tetrahydrofuran was added dropwise to a suspension of 0.9 g of lithium alu-

Table 2

| Test Compounds | Levallorphan Antagonism for mouse (Acetic Acid Method) | Continuous Administration (3 weeks) for rats | |
|---|---|---|---|
| | | Weight reduction by discontinuous administration | Weight reduction by Levallorphan antagonism |
| (±) form · $C_3H_6O_3$ | ++ | + | ++ |
| (+) form · $C_3H_6O_3$ | − | − | − |
| (−) form · $C_3H_6O_3$ | + | − | + |
| Morphino . HCl | +++ | +++ | +++ |

Remarks:
the symbol (−) shows no effect.
The symbols (+), (++) and (+++) show the degree of effect in an increasing order.

EXAMPLE 1

(1) 2-(4-Methoxyphenyl)-2-methylpropanal-1 (70 g) and urethane (73 g) were dissolved in benzene (500 ml), and after the addition of 1 ml of boron trifluoride etherate, the mixture was refluxed for 5 hours with a reflux minium hydride in 5 ml of dried tetrahydrofuran while stirring under cooling with ice and then the mixture was refluxed for 30 minutes. After cooling, water-containing ether (150 ml) and then 10 ml of a 30% sodium hydroxide aqueous solution was added dropwise to the mixture while stirring under cooling with ice. An diethyl ether-tetrahydrofuran layer was decanted and combined with the diethyl ether portions with which the remaining matter had been washed. The combined liquid was dried over potassium carbonate, stripped of the solvent and distilled under reduced pressure to obtain 2.1 g of 1,2,3,6-tetrahydro-2-[1-(4-methoxyphenyl)-1-methylethyl]-1,4-dimethylpyridine as a colorless viscous mass.

(b.p.: 115°–117° C./0.4 mmHg).

Analysis: Calcd. for $C_{17}H_{25}ON$: C, 78.71; H, 9.72; N, 5.40 (%). Found: C, 78.81; H, 10.14; N, 5.45 (%).

(4) A mixture of 2.6 g of 1,2,3,6-tetrahydro-2-[1-(4-methoxyphenyl)-1-methylethyl]-1,4-dimethylpyridine, 30 ml of 47% hydrobromic acid and 10 ml of acetic acid was refluxed for 12 hours while stirring. After cooling, the reaction mixture was made alkaline with concentrated ammonia water under cooling and then extracted with chloroform. The extract was washed with water, dried over sodium sulfate, stripped of chloroform and recrystallized from chloroform-hexane to obtain 2.0 g of 1,2,3,4,5,6-hexahydro-8-hydroxy-2,6-methano-1,1,3,6-tetramethyl-3-benzazocine as pale orange cubes.

(m.p.: 182°–184° C.).

Analysis: Calcd. for $C_{16}H_{23}ON$: C, 78.32; H, 9.45; N, 5.71 (%). Found: C, 78.44; H, 9.49; N, 5.61 (%).

(5) The resulting product in the form of free base was dissolved in diethyl ether and to the solution was added a saturated hydrogen chloride in diethyl ether to render the precipitation in the form of its hydrochloride. The precipitated crystals were recovered by the filtration and then recrystallized from methanol-ethyl ether to obtain reddish brown prisms.

(m.p.: 270°–272° C.).

Analysis: Calcd. for $C_{16}H_{24}ONCl$: C, 68.19; H, 8.58; N, 4.97 (%). Found: C, 67.89; H, 8.73; N, 4.94 (%).

The following compounds shown in Table 3 were prepared in a manner similar to that described above.

Table 3

| No. | Compounds | Appearance melting point (°C.) or boiling point (°C./mmHg) | Analysis: Calcd.: C(%); H(%); N(%) Found: C(%); H(%); N(%) |
|---|---|---|---|
| 1 | (structure) | Colorless syrup 103–105/0.4 | $C_{17}H_{25}N$ 83.89  10.35  5.76 83.80  10.21  5.73 |
| 2 | Compound 1 (hydrochloride) | Colorless needles above 260 (sublimable) | $C_{17}H_{26}NCl$ 72.96  9.36  5.01 73.00  9.40  5.00 |
| 3 | (structure) · HBr | Colorless prisms 253–254 | $C_{16}H_{22}NCl \cdot HBr$ 55.75  6.73  4.06 55.56  6.74  3.80 |
| 4 | (structure) · HCl | Colorless prisms above 250 (sublimable) | $C_{16}H_{23}NCl_2$ 64.00  7.72  4.66 63.85  7.70  4.60 |
| 5 | (structure) | Pale yellow syrup 100–102/0.8 | $C_{16}H_{23}N$ 83.78  10.11  6.11 83.81  10.32  6.05 |
| 6 | Compound 5 (hydrochloride) monohydrate | Colorless plates above 250 (sublimable) | $C_{16}H_{24}NCl \cdot H_2O$ 67.70  9.23  4.93 67.90  9.49  5.21 |
| 7 | (structure) | Pale red needles 187–189 | $C_{17}H_{25}ON$ 78.71  9.72  5.40 78.83  9.96  5.51 |
| 8 | Compound 7 (oxalate) | Yellow granules above 250 (sublimable) | $C_{19}H_{27}O_5N$ 65.31  7.79  4.01 65.24  8.07  4.06 |

Table 3-continued

| No. | Compounds | Appearance melting point (°C.) or boiling point (°C./mmHg) | Analysis: Calcd.: C(%); H(%); N(%) / Found: C(%); H(%); N(%) |
|---|---|---|---|
| 9 | (structure: 6-hydroxy-1,1,4-trimethyl-tetrahydronaphthalene with N(CH$_3$)CH(CH$_3$) side chain) | Pale brown granules 147–148 | $C_{17}H_{25}ON$ <br> 78.71 9.72 5.40 <br> 78.75 9.86 5.40 |
| 10 | Compound 9 (oxalate) | Pale brown granules 228 (decomposition) | $C_{19}H_{27}O_5N$ <br> 65.31 7.79 4.01 <br> 65.33 7.99 4.14 |
| 11 | (structure: 6-chloro analog with N(CH$_3$) side chain · HCl) | Colorless granules 247 (decomposition) | $C_{17}H_{25}NCl_2 \cdot \tfrac{1}{2}H_2O$ <br> 63.15 8.11 4.33 <br> 63.10 8.13 4.35 |
| 12 | (structure: 6-chloro analog, different stereochemistry · HCl) | Colorless needles above 230 (sublimable) | $C_{17}H_{25}NCl_2$ <br> 64.96 8.02 4.46 <br> 64.69 8.04 4.40 |
| 13 | (structure: spirocyclopentane, 6-hydroxy, N-CH$_3$ · HCl) | Pale red granules 253 (decomposition) | $C_{18}H_{26}ONCl$ <br> 70.22 8.51 4.55 <br> 69.99 8.55 4.45 |
| 14 | (structure: 6-hydroxy-1,1,4-trimethyl tetrahydronaphthalene with N(CH$_3$)CH(CH$_3$), different stereochem) | Colorless prisms 164–165 | $C_{17}H_{25}ON$ <br> 78.71 9.72 5.40 <br> 78.79 9.69 5.43 |
| 15 | Compound 14 (oxalate) | Colorless granules 233 (decomposition) | $C_{19}H_{27}O_5N$ <br> 65.31 7.79 4.01 <br> 65.18 7.74 3.96 |
| 16 | (structure: spirocyclohexane, 6-hydroxy, N-CH$_3$ · HCl) | Pale green prisms 285 (decomposition) | $C_{19}H_{28}ONCl$ <br> 70.90 8.77 4.35 <br> 70.69 8.90 4.41 |
| 17 | (structure: spirocyclopentane, 6-hydroxy, N(CH$_3$)CH(CH$_3$) · oxalate (COOH)$_2$) | Colorless prisms 243 (decomposition) | $C_{21}H_{29}O_5N$ <br> 67.18 7.79 3.73 <br> 67.15 8.01 3.75 |

Table 3-continued

| No. | Compounds | Appearance melting point (°C.) or boiling point (°C./mmHg) | Analysis: Calcd.: C(%); H(%); N(%) Found: C(%); H(%); N(%) |
|---|---|---|---|
| 18 | [structure: spiro cyclopentane-tetrahydronaphthalene with HO-, CH3, N-CH3, CH3, CH3·C(COOH)2 substituents] | Pale brown granules 223 (decomposition) | C21H29O5N 67.18 7.79 3.73 67.05 8.00 3.78 |
| 19 | [structure: spiro cyclopentane tetrahydronaphthalene with OH, N-CH3, phenyl substituents] | Pale brown granules 112 (decomposition) | C23H27ON 82.84 8.16 4.20 82.80 8.15 4.15 |
| 20 | Compound 19 (hydrochloride) | Pale red prisms 283–286 | C23H28ONCl 74.68 7.63 3.79 74.43 7.78 3.75 |
| 21 | Compound 19 (oxalate) | Pale brown granules above 250 (sublimable) | C25H29O5N 70.90 6.90 3.31 70.71 6.85 3.14 |
| 22 | [structure: tetrahydronaphthalene with CH3, CH3, HO-, N-CH3, phenyl substituents] | Colorless needles 210–212 | C21H25ON 82.04 8.20 4.56 82.00 8.15 4.59 |
| 23 | Compound 22 (hydrochloride) | Colorless needles 282 (decomposition) | C21H26ONCl 73.34 7.62 4.07 73.31 7.71 3.97 |
| 24 | [structure: spiro cyclopentane tetrahydronaphthalene with Cl, N-CH3, phenyl substituents] | Colorless needles 254–256 | C23H27NCl2 71.13 7.01 3.61 71.01 7.16 3.60 |

EXAMPLE 2

A mixture of 1-ethoxycarbonyl-1,2,3,6-tetrahydro-2-[1-(4-chlorophenyl)-1-methylethyl]-4-methylpyridine (14.5 g), sodium hydroxide (15 g) and diethylene glycol (150 ml) was refluxed for 5 hours. After cooling, water was added to the reaction mixture and the resulting mixture was extracted with benzene. The extract was washed with water and dried over potassium carbonate. After removal of benzene, the residue was distilled under reduced pressure to obtain 10.7 g of a colorless viscous mass of 2-[1-(4-chlorophenyl)-1-methylethyl]-1,2,3,6-tetrahydro-4-methylpyridine.

(m.p.: 136°–138° C./0.6 mmHg)

The product (6.5 g) was dissolved in 40 ml of 47% hydrobromic acid and refluxed for 10 hours. After cooling, the reaction mixture was alkalized with concentrated ammonia water and extracted with benzene. The extract was dried over potassium carbonate and distilled to remove benzene. The residue was fed into a silica gel column chromatograph and eluted with chloroform-methanol (100:1). The solvent was distilled off from the eluant to obtain 3.3 g of 8-chloro-1,2,3,4,5,6-hexahydro-2,6-methanol-1,1,6-trimethyl-3-benzazocine as a colorless viscous mass.

The product was treated as in Example 1-(5) to give the corresponding hydrochloride as colorless needles having a melting point above 250° C. (sublimable) as colorless needles.

Analysis: Calcd. for C15H21NCl2: C, 62.94; H, 7.39; N, 4.89 (%). Found: C, 62.68; H, 7.27; N, 5.04 (%).

The following two compounds were prepared in the same manner as above.

| | |
|---|---|
| (i) 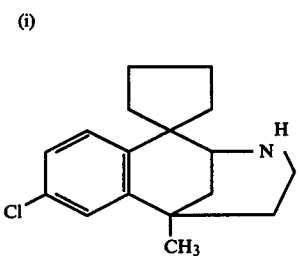 | Colorless syrup<br>b.p. 140–143° C./0.5 mmHg<br>Analysis: for C₁₇H₂₂NCl<br>        C      H      N<br>Calcd.: 74.03  8.04  5.08(%)<br>Found: 73.84  8.23  4.97(%) |
| (ii) 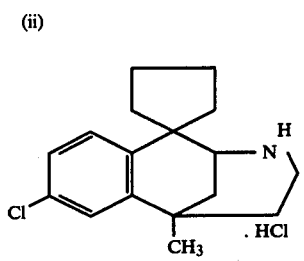 | Colorless needles<br>m.p. above 280° C. (sublimable)<br>Analysis: for C₁₇H₂₃NCl₂<br>        C      H      N<br>Calcd.: 65.38  7.42  4.49(%)<br>Found: 65.52  7.57  4.47(%) |

EXAMPLE 3

A mixture of 1-ethoxycarbonyl-1,2,3,6-tetrahydro-4-methyl-2-[1-methyl-1-(4-methylphenyl)ethyl]pyridine (4.2 g) and 40 ml of 47% hydrobromic acid was refluxed for 10 hours while stirring. After cooling, the mixture was made alkaline with a 10% sodium hydroxide aqueous solution and extracted with benzene. The extract was dried over potassium carbonate and benzene was distilled off. The residue was distilled under reduced pressure to give 3.0 g of 1,2,3,4,5,6-hexahydro-2,6-methano-1,1,6,8-tetramethyl-3-benzazocine as colorless oil.

(b.p.: 107°–109° C./0.3 mmHg)

Analysis: Calcd. for C₁₆H₂₃N: C, 83.73; H, 10.11; N, 6.11 (%). Found: C, 83.55; H, 10.11; N, 6.00 (%).

The product was treated as in Example 1-(5) to obtain the corresponding hydrochloride having a melting point above 250° C. (sublimable) as colorless prisms.

Analysis: Calcd. for C₁₆H₂₄NCl: C, 72.29; H, 9.10; N, 5.27 (%). Found: C, 72.46; H, 9.11; N, 5.02 (%).

The following two compounds were prepared in the same manner as above.

| | |
|---|---|
| (ii) 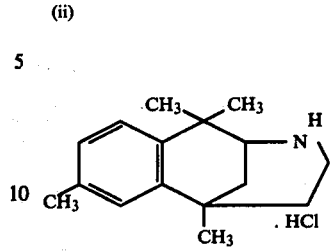 | Pale brown prisms<br>m.p. above 250° C. (sublimable)<br>Analysis: for C₁₆H₂₄NCl<br>        C      H      N<br>Calcd.: 72.29  9.10  5.27(%)<br>Found: 72.46  9.11  5.02(%) |

EXAMPLE 4

(1) A mixture of 1-ethoxycarbonyl-1,2,3,6-tetrahydro-2-[1-(4-methoxyphenyl)-1-methylethyl]-4-methylpyridine (6.34 g) and boron trifluoride etherate (10 ml) was maintained at a temperature ranging from 70° to 80° C. for 4 hours while stirring. After cooling, ice-water was added to the reaction mixture and then the mixture was extracted with benzene. The extract was washed three times with water and then two times with a saturated sodium bicarbonate aqueous solution and dried over potassium carbonate. After removal of benzene, the residue was further distilled under reduced pressure to obtain 6 g of 3-ethoxycarbonyl-1,2,3,4,5,6-hexahydro-2,6-methano-8-methoxy-1,1,6-trimethyl-3-benzazocine as a pale yellow syrup.

(b.p.: 162°–164° C./0.7 mmHg)

Analysis: Calcd. for C₁₉H₂₇O₃N: C, 71.89; H, 8.57; N, 4.41 (%). Found: C, 72.12; H, 8.64; N, 4.51 (%).

(2) A mixture of the resulting product, 3-ethoxycarbonyl-1,2,3,4,5,6-hexahydro-2,6-methano-8-methoxy-1,1,6-trimethyl-3-benzazocine (30 g), 47% hydrobromic acid (80 ml) and acetic acid (80 ml) was refluxed for 2 hours while stirring. After cooling, the reaction mixture was made alkaline with a concentrated ammonia water while cooling with ice and the resulting precipitate was recovered by the filtration, dried with air and recrystallized from methanol to obtain 16.3 g of 1,2,3,4,5,6-hexahydro-8-hydroxy-2,6-methano-1,1,6-trimethyl-3-benzazocine as colorless granules.

(m.p.: 255°–257° C.).

Analysis: Calcd. for C₁₅H₂₁ON: C, 77.88; H, 9.15; N, 6.05 (%). Found: C, 77.62; H, 9.15; N, 6.15 (%).

The following compounds were prepared in the same manner as above.

| | |
|---|---|
| (i) 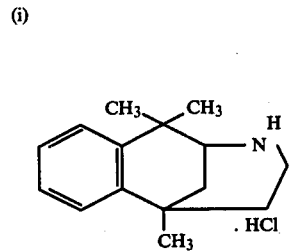 | Colorless fine needles<br>m.p. above 290° C. (sublimable)<br>Analysis: for C₁₅H₂₂NCl<br>        C      H      N<br>Calcd.: 71.55  8.81  5.56(%)<br>Found: 71.30  8.65  5.22(%) |
| (i) 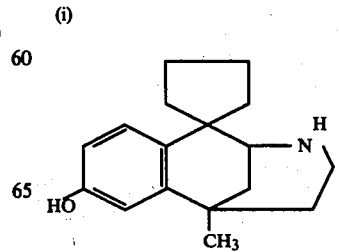 | Colorless granules<br>m.p. 254–256° C.<br>Analysis: for C₁₇H₂₃ON<br>        C      H      N<br>Calcd.: 79.33  9.01  5.44(%)<br>Found: 79.30  9.15  5.30(%) |

| | |
|---|---|
| (ii) 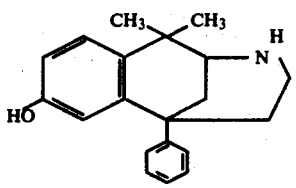 | Colorless granules<br>m.p. 257–259° C.<br>Analysis: for $C_{20}H_{23}ON$<br>　　　　C　　　H　　　N<br>Calcd.: 81.87　7.90　4.77(%)<br>Found: 81.78　7.82　4.80(%) |

EXAMPLE 5

(1) A mixture of 1-(1-ethoxycarbonyl-1,2,3,6-tetrahydro-4-methylpyridine-2-yl)-1-(4-chlorophenyl)cryclopentane (6.8 g) and 47% hydrobromic acid (60 ml) was heated to reflux for 10 hours while stirring. After cooling, the reaction mixture was made alkaline with a 10% sodium hydroxide aqueous solution and extracted with benzene. The extract was dried over potassium carbonate and distilled to remove benzene. The residue was further distilled under reduced pressure to obtain 4.1 g of 8-chloro-1,2,3,4,5,6-hexahydro-2,6-methano-6-methyl-3-benzazocine-1-spiro-1'-cyclopentane as colorless oil.

(b.p.: 140°–143° C./0.5 mmHg).

Analysis: Calcd. for $C_{17}H_{22}NCl$: C, 74.03; H, 8.04; N, 5.08 (%). Found: C, 73.84; H, 8.13; N, 4.97 (%).

The resulting product was treated as in Example 1-(5) to obtain the corresponding hydrochloride as colorless fine needles having a melting point above 270° C. and being sublimable (after recrystallization from methanol-diethyl ether).

Analysis: Calcd. for $C_{17}H_{23}NCl_2$: C, 65.38; H, 7.42; N, 4.49 (%). Found: C, 65.62; H, 7.57; N, 4.47 (%).

(2) The resulting product, 8-chloro-1,2,3,4,5,6-hexahydro-2,6-methano-6-methyl-3-benzazocine-1-spiro-1'-cyclopentane (4 g) was dissolved in 40 ml of methanol and to the solution was added 5 ml of 37% aqueous formaldehyde and then 0.7 g of sodium borohydride was slowly added under cooling with ice while stirring. After further stirring the mixture at room temperature for one hour, the solvent was distilled off from the mixture and the residue, after adding water, was extracted with benzene. The extract was dried over potassium carbonate and distilled to remove benzene to obtain 4.1 g of 8-chloro-1,2,3,4,5,6-hexahydro-2,6-methano-3,6-dimethyl-3-benzazocine-1-spiro-1'-cyclopentane as colorless oil. The product was further treated as in Example 1-(5) to obtain the corresponding hydrochloride as colorless fine needles having a melting point above 270° C. and being sublimable after recrystallization from methanol-ethyl ether.

Analysis: Calcd. for $C_{18}H_{25}NCl_2$: C, 66.25; H, 7.72; N, 4.29 (%). Found: C, 66.46; H, 7.74; N, 4.38 (%).

EXAMPLE 6

A mixture of 1,2,3,6-tetrahydro-2-[1-(4-methoxyphenyl)-1-methylethyl]-4-methylpyridine (2.9 g), pentyl iodide (2.34 g), potassium carbonate (3 g) and dimethylformamide (20 ml) was heated to reflux for 4 hours while stirring. After cooling and adding water, the reaction product was extracted with benzene. The extract was washed twice with water, dried over potassium carbonate and distilled to remove benzene to obtain 2.8 g of 1,2,3,6-tetrahydro-1-pentyl-2-[1-(4-methoxyphenyl)-1-methylethyl]-4-methylpyridine as a viscous mass. To the mass was added 20 ml of 47% hydrobromic acid and the mixture was heated to reflux for 10 hours while stirring, after cooling, made alkaline with a concentrated ammonia water under cooling and extracted with chloroform. The extract was dried over sodium sulfate and distilled to remove chloroform. The residue was fed to a column chromatograph on silica gel and eluted with chloroform. Chloroform was distilled off from the eluate to obtain 2.2 g of 1,2,3,4,5,6-hexahydro-8-hydroxy-3-pentyl-2,6-methano-1,1,6-trimethyl-3-benzazocine as a viscous mass. The product was treated as in Example 1-(5) to obtain the corresponding hydrochloride as colorless fine needles having a melting point above 230° C. (sublimable) after the recrystallization from methanol-ethyl ether.

Analysis: Calcd. for $C_{20}H_{32}ONCl$: C, 71.08; H, 9.54; N, 4.14 (%). Found: C, 69.95; H, 9.58; N, 4.36 (%).

The following compounds were prepared in a manner similar to that described above.

| | |
|---|---|
| (i) 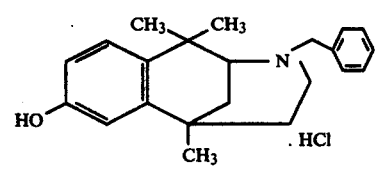 | Pale brown granules<br>m.p. 257–260° C.<br>Analysis: for $C_{22}H_{28}ONCl$<br>　　　　C　　　H　　　N<br>Calcd.: 73.83　7.89　3.91(%)<br>Found: 73.92　8.00　4.05(%) |
| (ii) 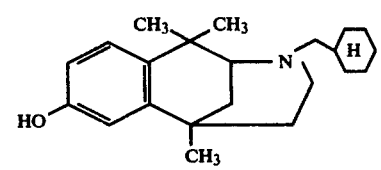 | Pale brown needles<br>m.p. above 250° C.<br>Analysis: for $C_{22}H_{33}ON \cdot CHCl_3$<br>　　　　C　　　H　　　N<br>Calcd.: 61.98　7.66　3.13(%)<br>Found: 62.02　7.89　3.41(%) |

EXAMPLE 7

A mixture of 2.5 g of 1-ethoxycarbonyl-1,2,3,6-tetrahydro-2-[1-methyl-1-(3,4,5-trimethoxyphenyl)ethyl]-4-methylpyridine, 1.4 g of para-toluene sulfonic acid hydrate and 50 ml of dried benzene was heated to reflux for 2 hours while stirring and, after cooling, washed twice with water and once with a saturated sodium bicarbonate aqueous solution and then dried over potassium carbonate. Benzene was distilled off from the reaction mixture to obtain 2.5 g of 3-ethoxycarbonyl-1,2,3,4,5,6-hexahydro-2,6-methano-7,8,9-trimethoxy-1,1,6-trimethyl-3-benzazocine. The product was dissolved in 20 ml of tetrahydrofuran and the solution was added dropwise to a suspension of 0.8 g of lithium aluminium hydride in 5 ml of tetrahydrofuran while stirring under cooling with ice, followed by refluxing for 30 minutes. After cooling, to the mixture was added 100 ml of ethyl ether containing water while stirring under cooling with ice to decompose excess lithium aluminium hydride and then was added a 10% sodium hydroxide aqueous solution. The supernatant was recovered by the decantation and combined with the remaining residue after it had been washed with diethyl ether. The mixture was dried over potassium carbonate and distilled to remove the solvent to obtain 2.0 g of viscous mass. The mass was purified through column chromatograph on silica gel and then recrystallized from diethyl ether to obtain 1 g of 1,2,3,4,5,6-hexahydro-2,6-methano-7,8,9-trimethoxy-1,1,3,6-tetramethyl-3-benzazocine as colorless needles.
(m.p.: 68°–70° C.).

Analysis: Calcd. for $C_{19}H_{29}O_3N$: C, 71.44; H, 9.15; N, 4.39 (%). Found: C, 71.58; H, 9.24; N, 4.30 (%).

The product obtained above was treated as in Example 1-(5) to obtain the corresponding hydrochloride as colorless silky needles.
(m.p.: 265°–267° C., (foaming upon melting)).
Analysis: Calcd. for $C_{19}H_{30}O_3NCl$: C, 64.12; H, 8.50; N, 3.94 (%). Found: C, 64.00; H, 8.50; N, 3.82 (%).

EXAMPLE 8

A mixture of 5.0 g of 1-(1-ethoxycarbonyl-1,2,3,6-tetrahydro-4-methylpyridine-2-yl)-1-(4-methoxyphenyl)-cyclopropane and 11 ml of boron trifluoride etherate was heated to 70° C. for 3.5 hours while stirring and, after cooling, extracted with benzene. The extract was washed three times with ice-water and then twice with a saturated sodium bicarbonate aqueous solution, dried over potassium carbonate and distilled to remove benzene to obtain 4.2 g of residue. The residue was treated as in Example 7 by the use of 1.2 g of lithium aluminium hydride to obtain 1.8 g of 1,2,3,4,5,6-hexahydro-2,6-methano-8-methoxy-3,6-dimethyl-3-benzazocine-1-spiro-1'-cryclopropane. The product was treated as in Example 1-(5) to obtain the corresponding hydrochloride as pale brown needles.
(m.p.: 266°–268° C.).
Analysis: Calcd. for $C_{11}H_{24}ONCl$: C, 69.49; H, 8.23; N, 4.77 (%). Found: C, 69.30; H, 8.14; N, 4.65 (%).

The following compounds were prepared in the manner disclosed above.

(i) 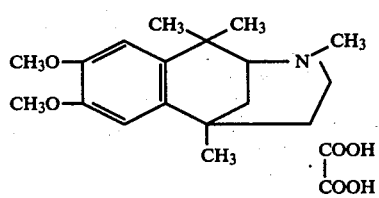

Colorless granules
m.p. 240–242° C. (foaming upon melting)
Analysis: for $C_{20}H_{29}O_2N$

| | C | H | N |
|---|---|---|---|
| Calcd.: | 63.30 | 7.70 | 3.69(%) |
| Found: | 63.16 | 7.72 | 3.82(%) |

(ii) 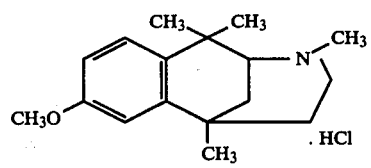

Colorless prisms
m.p. 251–253° C.
Analysis: for $C_{17}H_{26}ONCl$

| | C | H | N |
|---|---|---|---|
| Calcd.: | 69.01 | 8.86 | 4.73(%) |
| Found: | 69.12 | 9.02 | 4.60(%) |

(iii) 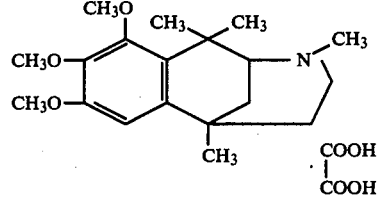

Colorless needles
m.p. 265° C. (decomposition)
Analysis: for $C_{21}H_{31}O_7N$

| | C | H | N |
|---|---|---|---|
| Calcd.: | 61.59 | 7.63 | 3.42(%) |
| Found: | 61.38 | 7.62 | 3.43(%) |

EXAMPLE 9

(1) 4-(1-Ethoxycarbonyl-1,2,3,6-tetrahydro-4-methyl-pyridine-2-yl)-4-(4-methoxyphenyl)-tetrahydropyran (4.2 g) was treated as in Example 8 to obtain 3.4 g of 1,2,3,4,5,6-hexahydro-2,6-methano-8-methoxy-3,6-dimethyl-3-benzazocine-1-spiro-4'-tetrahydropyran as colorless prisms.

(m.p.: 149°–150° C.; after recrystallization from methanol).

Analysis: Calcd. for $C_{19}H_{27}O_2N$: C, 75.71; H, 9.03; N, 4.65 (%). Found: C, 75.68; H, 9.22; N, 4.80 (%).

(2) The product in the form of a base was dissolved in ethyl ether and to the solution was added a saturated solution of oxalic acid in ethyl ether to form precipitates. The precipitates were recrystallized from methanol-ethyl ether to obtain the corresponding oxalate as colorless plates.

(m.p.: 253° C. (decomposition)).

Analysis: Calcd. for $C_{21}H_{29}O_6N$: C, 64.43; H, 7.47; N, 3.58 (%). Found: C, 64.62; H, 7.63; N, 3.79 (%).

(3) A mixture of the product obtained in (1) above (1 g) and pyridine hydrochloride (20 g) was refluxed on a bath having a temperature of 200° C. for 30 minutes while stirring. After cooling, water was added to the reaction mixture and then the mixture was made alkaline with ammonia and extracted with benzene. The extract was thoroughly washed with water, dried over potassium carbonate and distilled to remove benzene. Ethanol and toluene were added to the residue and distilled to remove pyridine with the added solvents. The residue was purified through a column chromatograph on silica gel to obtain 0.5 g of 1,2,3,4,5,6-hexahydro-8-hydroxy-2,6-methano-3,6-dimethyl-3-benzazocine-1-spiro-4'-tetrahydropyran as a glassy mass. The product was treated as in (2) above to obtain the corresponding oxalate as pale brown needles.

(m.p.: 247° C. (decomposition)).

Analysis: Calcd. for $C_{20}H_{27}O_6N$: C, 63.64; H, 7.21; N, 3.71 (%). Found: C, 63.65; H, 7.43; N, 3.68 (%).

EXAMPLE 10

1-Ethoxycarbonyl-1,2,3,6-tetrahydro-2-[1-methyl-1-(3,4-methylene-dioxyphenyl)ethyl]-4-methylpyridine (2.9 g) was cyclized and reduced by the use of 2.0 g p-toluenesulfonic acid monohydrate, 55 ml of dried benzene and 0.7 g of lithium aluminum hydride as in Example 7 and recrystallized from chloroform-hexane to obtain 1,2,3,4,5,6-hexahydro-2,6-methano-1,1,3,6-tetramethyl-8,9-methylenedioxy-3-benzazocine as colorless needles.

(m.p.: 156°–158° C.).

Analysis: Calcd. for $C_{17}H_{23}O_2N$: C, 74.69; H, 8.48; N, 5.12 (%). Found: C, 74.85; H, 8.43; N, 5.09 (%).

The resulting product was treated as in Example 1-(5) to obtain the corresponding hydrochloride monohydrate.

(m.p.: 264°–266° C.).

Analysis: Calcd. for $C_{17}H_{24}O_2NCl$: C, 62.28; H, 7.99; N, 4.27 (%). Found: C, 62.36; H, 7.86; N, 4.11 (%).

EXAMPLE 11

A mixture of 1 g of 1,2,3,4,5,6-hexahydro-8-hydroxy-2,6-methano-1,1,6-trimethyl-3-benzazocine, 0.66 g of cinnamyl chloride, 0.3 g of sodium iodide, 1 g of potassium carbonate and 20 ml of dimethylformamide was refluxed for 3 hours while stirring and, after cooling and adding water, extracted with benzene. The extract was washed twice with water, dried over potassium carbonate and distilled to remove benzene. The residue was fed to a column chromatograph on silica gel and the fraction eluted by a solvent of chloroform or chloroform-methanol (100:1) was collected. By distillating off the solvent from the fraction, 1.3 g of reddish brown viscous mass was obtained. A small amount of diethyl ether was added to the mass and the mixture was allowed to stand to deposit crystals. The crystals were recovered by filtration and recrystallized from chloroform-hexane to obtain 3-cinnamyl-1,2,3,4,5,6-hexahydro-8-hydroxy-2,6-methano-1,1,6-trimethyl-3-benzazocine as pale yellow plates.

(m.p.: 86°–88° C.).

Analysis: Calcd. for $C_{24}H_{29}ON$: C, 82.95; H, 8.41; N, 4.03 (%). Found: C, 82.81; H, 8.53; N, 4.00 (%).

The product in the form of free base was dissolved in methanol followed by adding a saturated hydrogen chloride solution in ethyl ether. The deposited crystals were recovered by the filtration and recrystallized from methanol-ether to obtain the corresponding hydrochloride as pale yellow needles.

(m.p.: 188° C. (decomposition)).

Analysis Calcd. for $C_{24}H_{30}ONCl \cdot \frac{1}{2}H_2O$: C, 73.35; H, 7.95; N, 3.56 (%). Found: C, 73.40; H, 7.93; N, 3.60 (%).

The following compounds shown in Table 4 were prepared in the same manner as above.

Table 4

| No. | Compounds | Appearance melting point (°C.) or boiling point (°C./mmHg) | Analysis: Calcd.: C(%); H(%); N(%) Found: C(%); H(%); N(%) |
|---|---|---|---|
| 1 | (structure with CH₃, CH₃, CH₃, CH₃ substituents, N, ·HCl) | Colorless plates above 230 (sublimable) | $C_{20}H_{30}NCl$ 75.09  9.45  4.38 74.99  9.40  4.53 |
| 2 | (structure with CH₃, CH₃, CH₃, Cl substituents, N, ·HCl) | Colorless needles above 230 (sublimable) | $C_{19}H_{27}NCl_2$ 67.05  8.00  4.11 66.89  8.04  4.27 |

Table 4-continued

| No. | Compounds | Appearance melting point (°C.) or boiling point (°C./mmHg) | Analysis: Calcd.: C(%); H(%); N(%) Found: C(%); H(%); N(%) |
|---|---|---|---|
| 3 | (structure: 6-Cl, gem-diMe, CH3, N-CH2CH=CH2 · HCl) | Colorless needles above 230 (sublimable) | C₁₈H₂₅NCl₂ 66.25  7.72  4.29 66.41  7.87  4.06 |
| 4 | (structure: 6-HO, gem-diMe, CH3, N-cyclopropyl · HCl) | Colorless granules 197 (decomposition) | C₁₉H₂₈ONCl · H₂O 67.14  8.90  4.12 67.40  9.10  4.18 |
| 5 | (structure: 6-HO, gem-diMe, CH3, N-CH2CH=CH2 · HCl) | Colorless leaves 237 (decomposition) | C₁₈H₂₆ONCl 70.22  8.51  4.55 70.01  8.45  4.63 |
| 6 | (structure: 6-HO, gem-diMe, CH3, N-(CH2)3-CO-C6H4-F, ·COOH-COOH) | Pale yellow prisms 120 (decomposition) | C₂₇H₃₂O₆NF 66.79  6.64  2.88 67.00  6.70  2.99 |
| 7 | (structure: 6-Cl, gem-diMe, CH3, N-(CH2)3-CO-C6H4-F, ·COOH-COOH) | Colorless granules 214 (decomposition) | C₂₇H₃₁O₅NFCl 64.34  6.20  2.78 64.26  6.18  2.89 |
| 8 | Compound 7 (hydrochloride) | Colorless prisms 196–198 | C₂₅H₃₀ONFCl₂ 66.66  6.71  3.11 66.86  6.50  3.34 |
| 9 | (structure: gem-diMe, CH3, N-(CH2)3-CO-C6H4-F · HCl) | Colorless granules 223–225 | C₂₅H₃₁ONFCl 72.18  7.51  3.37 72.23  7.61  3.53 |
| 10 | (structure: CH3 on ring, gem-diMe, CH3, N-(CH2)3-CO-C6H4-F · HCl) | Colorless needles 201–203 | C₂₆H₃₂NOFCl 72.62  7.74  3.26 72.65  7.72  3.47 |
| 11 | (structure: 6-OH, gem-diMe, CH3, N-(CH2)2-C6H5 · HCl) | Colorless plates 233–235 | C₂₃H₃₀ONCl 74.27  8.13  3.76 74.25  8.13  3.72 |

Table 4-continued

| No. | Compounds | Appearance melting point (°C.) or boiling point (°C./mmHg) | Analysis: Calcd.: C(%); H(%); N(%) Found: C(%); H(%); N(%) |
|---|---|---|---|
| 12 | (structure: spirocyclopentane tetrahydronaphthalene with HO-, CH3, COOH/COOH substituents, N-CH2CH=CH2) | Pale brown prisms 205 (decomposition) | $C_{22}H_{29}O_5N$ 68.19  7.54  3.62 68.28  7.60  3.58 |
| 13 | (structure: dimethyl tetrahydronaphthalene with HO-, phenyl, N-CH2CH=CH2 · HCl) | Colorless needles 210 (changed to red) | $C_{23}H_{28}ONCl$ 74.68  7.63  3.79 74.47  7.65  3.79 |
| 14 | (structure: dimethyl tetrahydronaphthalene with HO-, phenyl, N-(CH2)2-phenyl) | Colorless needles 117–119 | $C_{28}H_{31}ON \cdot \frac{1}{4} CHCl_3$ 79.48  7.38  3.08 79.40  7.40  3.00 |
| 15 | Compound 14 (hydrochloride) | Colorless plates 205 (decomposition) | $C_{28}H_{32}ONCl \cdot H_2O$ 74.40  7.58  3.10 74.43  7.51  3.22 |
| 16 | (structure: spirocyclopentane with HO-, CH3, N-(CH2)2-phenyl · HCl) | Colorless needles 256–258 | $C_{25}H_{32}ONCl$ 75.45  8.10  3.52 75.28  8.24  3.64 |
| 17 | (structure: dimethyl tetrahydronaphthalene with HO-, phenyl, N-CH2-cyclopropyl · HCl) | Pale brown needles 278–281 | $C_{24}H_{29}ON \cdot HCl$ 75.08  7.88  3.65 74.92  8.00  3.69 |
| 18 | (structure: spirocyclopentane with HO-, CH3, N-CH2-cyclopropyl · HCl) | Colorless plates 276–278 | $C_{21}H_{30}ONCl$ 72.49  8.69  4.03 72.70  8.90  4.16 |
| 19 | (structure: dimethyl tetrahydronaphthalene with HO-, CH3, N-CH2-cyclobutyl · HCl) | Colorless prisms 253–255 | $C_{20}H_{30}ONCl \cdot H_2O$ 67.87  9.11  3.95 67.69  9.23  3.92 |

Table 4-continued

| No. | Compounds | Appearance melting point (°C.) or boiling point (°C./mmHg) | Analysis: Calcd.: C(%); H(%); N(%) Found: C(%); H(%); N(%) |
|---|---|---|---|
| 20 | (structure shown: spirocyclopentane-fused benzazocine with HO, CH₃, N-cinnamyl, ·HCl) | Colorless prisms 247 (decomposition) | $C_{26}H_{32}ONCl \cdot \frac{1}{2} H_2O$<br>74.53  7.94  3.34<br>74.71  7.93  3.19 |
| 21 | (structure shown: 1,1-dimethyl-4-phenyl benzazocine with HO, N-cinnamyl, ·HCl) | Pale brown prisms 269–272 | $C_{29}H_{32}ONCl$<br>78.09  7.23  3.14<br>77.97  7.39  3.18 |

EXAMPLE 12

A mixture of 9.5 g of 1,2,3,4,5,6-hexahydro-8-hydroxy-2,6-methano-1,1,3,6-tetramethyl-3-benzazocine which is the product of Example 1-(4) and 40 ml of acetic anhydride was held at 80° C. for 4 hours and then distilled under reduced pressure on a bath having a temperature of 50° C. to remove acetic anhydride and acetic acid. The residue was extracted with benzene and the extract was washed several times with a sodium bicarbonate aqueous solution and dried over sodium sulfate. The distillation off of benzene from the extract gave 8.9 g of 8-acetoxy-1,2,3,4,5,6-hexahydro-2,6-methano-1,1,3,6-tetramethyl-3-benzazocine as a viscous mass. The product was treated as in Example 9-(2) and recrystallized from acetone-diethyl ether to obtain the corresponding oxalate as colorless granules. (m.p.: 161° C. (decomposition)).

Analysis: Calcd. for $C_{20}H_{27}O_6N$: C, 63.64; H, 7.21; N, 3.71 (%). Found: C, 63.48; H, 7.16; N, 3.62 (%).

EXAMPLE 13

(1) 1,2,3,4,5,6-Hexahydro-8-hydroxy-2,6-methano-1,1,6-trimethyl-3-benzazocine (17.32 g) and 14.4 g of D-(-)-quinic acid were dissolved in 150 ml of 70% aqueous ethanol at an elevated temperature and the solution was allowed to stand at room temperature to deposit colorless fine crystals. The crystals were recovered by filtration, washed with a small amount of ethanol and recrystallized from 90% aqueous ethanol to obtain 12.5 g of prisms having a melting point of from 250°–252° C. The crystals (11.5 g) was dissolved in 100 ml of 50% aqueous ethanol and the solution was made alkaline with concentrated ammonia water and allowed to stand in a refrigerator overnight to deposit crystals. The crystals were recovered by filtration and recrystallized from methanol-chloroform to obtain 6.0 g of (−)-1,2,3,4,5,6-hexahydro-8-hydroxy-2,6-methano-1,1,6-trimethyl-3-benzazocine as colorless prisms having a melting point above 290° C.

Analysis: Calcd. for $C_{15}H_{21}ON$: C, 77.88; H, 9.15; N, 6.05 (%). Found: C, 77.69; H, 9.14; N, 6.25 (%).

$[\alpha]_D^{20} = -30.6°$ (C=1, methanol)

(2) The filtrate in the last step of (1) above was allowed to stand in a refrigerator overnight to deposit colorless cubes. The crystals were separated out by filtration and recrystallized from ethanol to obtain 9.8 g of colorless granules.

(m.p.: 236°–238° C.).

The crystals were dissolved in 100 ml of 50% aqueous ethanol and the solution was made alkaline with concentrated ammonia water and allowed to stand in a refrigerator overnight to deposit crystals. The crystals were separated out by filtration, and recrystallized from methanol-chloroform to obtain 4.5 g of (+)-1,2,3,4,5,6-hexahydro-8-hydroxy-2,6-methano-1,1,6-trimethyl-3-benzazocine as colorless prisms. (having a melting point above 290° C.)

Analysis: Calcd. for $C_{15}H_{21}ON$: C, 77.88; H, 9.15; N, 6.05 (%). Found: C, 77.82; H, 9.23; N, 6.24 (%).

$[\alpha]_D^{20} = +30.5°$ (C=1, methanol).

(3) A mixture of 2.31 g of (−)-1,2,3,4,5,6-hexahydro-8-hydroxy-2,6-methano-1,1,6-trimethyl-3-benzazocine (the product according to (1) above), 1.53 g of cinnamyl chloride, 0.5 g of sodium iodide, 2.0 g of potassium carbonate and 50 ml of dimethyl formamide was heated to reflux for 2 hours. After cooling, ice water was added to the reaction mixture and then extracted with benzene. The extract was washed twice with benzene, dried over potassium carbonate and distilled to remove benzene. The residue was dissolved in ethanol and to the solution was added HCL-ethanol to deposit crystals. The crystals were recoverd by filtration and recrystallized from methanol-ethanol to obtain 2.8 g of (−)-3-cynnamyl-1,2,3,4,5,6-hexahydro-8-hydroxy-2,6-methano-1,1,6-trimethyl-3-benzazocine hydrochloride as colorless needles.

(m.p.: 237°–239° C.).

Analysis: Calcd. for $C_{24}H_{30}ONCl$: C, 75.07; H, 7.87; N, 3.65; Cl, 9.23 (%). Found: C, 75.16; H, 7.94; N, 3.82; Cl, 9.22 (%).

$[\alpha]_D^{20} = -30.2°$ (C=1, methanol).

(4) The product of (2), (+)-1,2,3,4,5,6-hexahydro-8-hydroxy-2,6-methano-1,1,6-trimethyl-3-benzazocine (2.31 g) and cinnamyl chloride (1,53 g) were treated as in (3) above to obtain 2.9 g of (+)-3-cinnamyl- 1,2,3,4,5,6-hexahydro-8-hydroxy-2,6-methano-1,1,6-trimethyl-3-benzazocine hydrochloride as colorless needles.

(m.p.: 237°–239° C.).

Analysis: Calcd. for $C_{24}H_{30}ONCl$: C, 75.07; H, 7.87; N, 3.65; Cl, 9.23 (%). Found: C, 75.26; H, 8.17; N, 3.88; Cl, 9.29 (%).

$[\alpha]_D^{20} = +29.8°$ (C=1, methanol).

What is claimed is:

1. A benzazocine derivative selected from the group consisting of 1,2,3,4,5,6-hexahydro-8-hydroxy-2,6-methano-3,6-dimethyl-3-benzazocine-1-spiro-1'-cyclopentane; 1,2,3,4,5,6-hexahydro-8-hydroxy-2,6-methano-3,6-dimethyl-3-benzazocine-1-spiro-1'-cyclopropane; 1,2,3,4,5,6-hexahydro-8-hydroxy-2,6-methano-3,5,6-trimethyl-3-benzazocine-1-spiro-1'-cyclopentane; 1,2,3,4,5,6-hexahydro-8-hydroxy-2,6-methano-3-methyl-6-phenyl-3-benzazocine-1-spiro-1'-cyclopentane; 8-chloro-1,2,3,4,5,6-hexahydro-2,6-methano-3-methyl-6-phenyl-3-benzazocine-1-spiro-1'-cyclopentane; 8-chloro-1,2,3,4,5,6-hexahydro-2,6-methano-6-methyl-3-benzazocine-1-spiro-1'-cyclopentane; 1,2,3,4,5,6-hexahydro-8-hydroxy-2,6-methano-6-methyl-3-benzazocine-1-spiro-1'-cyclopentane; 8-chloro-1,2,3,4,5,6-hexahydro-2,6-methano-6-methyl-3-benzazocine-1-spiro-1'-cyclopentane; 8-chloro-1,2,3,4,5,6-hexahydro-2,6-methano-3,6-dimethyl-3-benzazocine-1-spiro-1'-cyclopentane; 1,2,3,4,5,6-hexahydro-2,6-methano-8-methoxy-3,6-dimethyl-3-benzazocine-1-spiro-1'-cyclopropane; 1,2,3,4,5,6-hexahydro-2,6-methano-8-methoxy-3,6-dimethyl-3-benzazocine-1-spiro-4'-tetrahydropyran; 1,2,3,4,5,6-hexahydro-8-hydroxy-2,6-methano-3,6-dimethyl-3-benzazocine-1-spiro-4'-tetrahydropyran; 1,2,3,4,5,6-hexahydro-2,6-methano-1,1,3,6-tetramethyl-8,9-methylenedioxy-3-benzazocine; 3-[4'-(4''-fluorophenyl)-4'-oxobutyl]-1,2,3,4,5,6-hexahydro-8-hydroxy-2,6-methano-1,1,6-trimethyl-3-benzazocine; 8-chloro-3-[4'-(4''-fluorophenyl)-4'-oxobutyl]-1,2,3,4,5,6-hexahydro-2,6-methano-1,1,6-trimethyl-3-benzazocine; 3-[4'-(4''-fluorophenyl)-4'-oxobutyl]-1,2,3,4,5,6-hexahydro-2,6-methano-1,1,6-trimethyl-3-benzazocine; 3-[4'-(4''-fluorophenyl)-4'-oxobutyl]-1,2,3,4,5,6-hexahydro-2,6-methano-1,1,6,8-tetramethyl-3-benzazocine; 3-allyl-1,2,3,4,5,6-hexahydro-8-hydroxy-2,6-methano-6-methyl-3-benzazocine-1-spiro-1'-cyclopentane; 1,2,3,4,5,6-hexahydro-8-hydroxy-2,6-methano-6-methyl-3-phenethyl-3-benzazocine-1-spiro-1'-cyclopentane; 3-cyclopropyl-methyl-1,2,3,4,5,6-hexahydro-8-hydroxy-6-methyl-3-benzazocine-1-spiro-1'-cyclopentane; and 3-cinnamyl-1,2,3,4,5,6-hexahydro-8-hydroxy-2,6-methano-6-methyl-3-benzazocine-1-spiro-1'-cyclopentane.

2. 1,2,3,4,5,6-Hexahydro-8-hydroxy-2,6-methano-3,6-dimethyl-3-benzazocine-1-spiro-1'-cyclopentane in according to claim 1.

3. 1,2,3,4,5,6-Hexahydro-8-hydroxy-2,6-methano-3,6-dimethyl-3-benzazocine-1-spiro-1'-cyclopropane in according to claim 1.

4. 1,2,3,4,5,6-Hexahydro-8-hydroxy-2,6-methano-3,5,6-trimethyl-3-benzazocine-1-spiro-1'-cyclopentane in according to claim 1.

5. 1,2,3,4,5,6-Hexahydro-8-hydroxy-2,6-methano-3-methyl-6-phenyl-3-benzazocine-1-spiro-1'-cyclopentane in according to claim 1.

6. 8-Chloro-1,2,3,4,5,6-hexahydro-2,6-methano-3-methyl-6-phenyl-3-benzazocine-1-spiro-1'-cyclopentane in according to claim 1.

7. 8-Chloro-1,2,3,4,5,6-hexahydro-2,6-methano-6-methyl-3-benzazocine-1-spiro-1'-cyclopentane in according to claim 1.

8. 1,2,3,4,5,6-Hexahydro-8-hydroxy-2,6-methano-6-methyl-3-benzazocine-1-spiro-1'-cyclopentane in according to claim 1.

9. 8-Chloro-1,2,3,4,5,6-hexahydro-2,6-methano-6-methyl-3-benzazocine-1-spiro-1'-cyclopentane in according to claim 1.

10. 8-Chloro-1,2,3,4,5,6-hexahydro-2,6-methano-3,6-dimethyl-3-benzazocine-1-spiro-1'-cyclopentane in according to claim 1.

11. 1,2,3,4,5,6-Hexahydro-2,6-methano-8-methoxy-3,6-dimethyl-3-benzazocine-1-spiro-1'-cyclopropane in according to claim 1.

12. 1,2,3,4,5,6-Hexahydro-2,6-methano-8-methoxy-3,6-dimethyl-3-benzazocine-1-spiro-1'-tetrahydropyran in according to claim 1.

13. 1,2,3,4,5,6-Hexahydro-8-hydroxy-2,6-methano-3,6-dimethyl-3-benzazocine-1-spiro-4'-tetrahydropyran in according to claim 1.

14. 1,2,3,4,5,6-Hexahydro-2,6-methano-1,1,3,6-tetramethyl-8,9-methylenedioxy-3-benzazocine in according to claim 1.

15. 3-[4'-(4''-Fluorophenyl)-4'-oxobutyl]-1,2,3,4,5,6-hexahydro-8-hydroxy-2,6-methano-1,1,6-trimethyl-3-benzazocine in according to claim 1.

16. 8-Chloro-3-[4'-(4''-fluorophenyl)-4'-oxobutyl]-1,2,3,4,5,6-hexahydro-2,6-methano-1,1,6-trimethyl-3-benzazocine in according to claim 1.

17. 3-[4'-(4''-Fluorophenyl)-4'-oxobutyl]-1,2,3,4,5,6-hexahydro-2,6-methano-1,1,6-trimethyl-3-benzazocine in according to claim 1.

18. 3-[4'-(Fluorophenyl)-4'-oxobutyl]-1,2,3,4,5,6-hexahydro-2,6-methano-1,1,6,8-tetramethyl-3-benzazocine in according to claim 1.

19. 3-Allyl-1,2,3,4,5,6-hexahydro-8-hydroxy-2,6-methano-6-methyl-3-benzazocine-1-spiro-1'-cyclopentane in according to claim 1.

20. 1,2,3,4,5,6-Hexahydro-8-hydroxy-2,6-methano-6-methyl-3-phenethyl-3-benzazocine-1-spiro-1'-cyclopentane in according to claim 1.

21. 3-Cyclopropylmethyl-1,2,3,4,5,6-hexahydro-8-hydroxy-6-methyl-3-benzazocine-1-spiro-1'-cyclopentane in according to claim 1.

22. 3-Cinnamyl-1,2,3,4,5,6-hexahydro-8-hydroxy-2,6-methano-6-methyl-3-benzazocine-1-spiro-1'-cyclopentane in according to claim 1.

* * * * *